(12) United States Patent
Dillon et al.

(10) Patent No.: US 6,626,884 B1
(45) Date of Patent: Sep. 30, 2003

(54) SAMPLING IN BLOOD COLLECTION

(75) Inventors: Jagmohanbir Singh Dillon, Oxley (AU); William Leonard Mobbs, Farrar (AU)

(73) Assignee: Noble House Group Pty. Ltd., Fyshwick (AU)

( * ) Notice: Subject to any disclaimer, the term of this patent is extended or adjusted under 35 U.S.C. 154(b) by 0 days.

(21) Appl. No.: 09/807,068

(22) PCT Filed: Oct. 25, 1999

(86) PCT No.: PCT/AU99/00918
§ 371 (c)(1), (2), (4) Date: Apr. 9, 2001

(87) PCT Pub. No.: WO00/24313
PCT Pub. Date: May 4, 2000

(30) Foreign Application Priority Data

Oct. 26, 1998 (AU) .............................................. PP6768

(51) Int. Cl.[7] .......................... A61B 19/00; A61M 1/00
(52) U.S. Cl. ...................... 604/409; 604/323; 604/248; 600/573
(58) Field of Search ........................... 604/409, 7, 323, 604/248, 249; 600/573

(56) References Cited

U.S. PATENT DOCUMENTS

| 3,327,709 | A | * | 6/1967 | Nehring et al. | |
| 3,654,924 | A | | 4/1972 | Wilson et al. | |
| 4,056,101 | A | | 11/1977 | Geissler et al. | |
| 4,423,741 | A | * | 1/1984 | Levy | 137/625.48 |
| 4,593,717 | A | * | 6/1986 | Levasseur | 137/556.6 |
| 4,786,286 | A | | 11/1988 | Cerny et al. | |
| 5,167,656 | A | | 12/1992 | Lynn | |
| 5,772,608 | A | * | 6/1998 | Dhas | 600/578 |
| 6,364,847 | B1 | * | 4/2002 | Shulze et al. | 600/573 |

FOREIGN PATENT DOCUMENTS

| EP | 0376168 A2 | 7/1990 |
| JP | 10211274 | 8/1998 |
| WO | WO 90/12606 | 11/1990 |
| WO | WO 94/12093 | 6/1994 |

* cited by examiner

*Primary Examiner*—Alfred Basichas
(74) *Attorney, Agent, or Firm*—Sidley Austin Brown & Wood LLP

(57) ABSTRACT

Methods and apparatus are disclosed whereby the initial flow of blood during blood collection is diverted to a sample pouch to trap the skin plug and to allow samples to be taken during subsequent blood collection to a normal blood bag. This is effected by connecting the needle line (106), the sample line (118) to the sample pouch (116) and the bag line (114) to the blood bag to a multi-port valve (110) that includes an actuator (120). During the procedure, the valve (110) may be attached to the arm (100) of the donor by means of a wrist-strap (112).

21 Claims, 8 Drawing Sheets

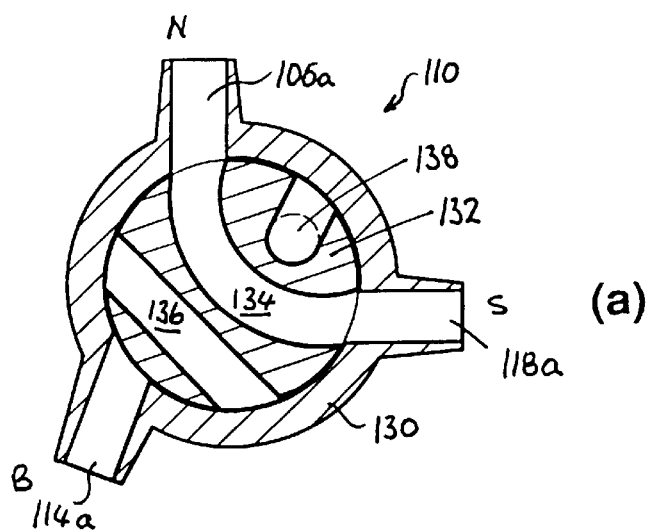
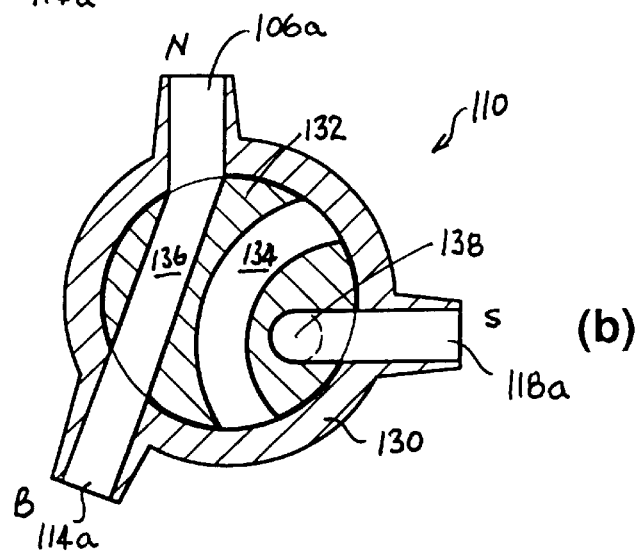
Fig. 2
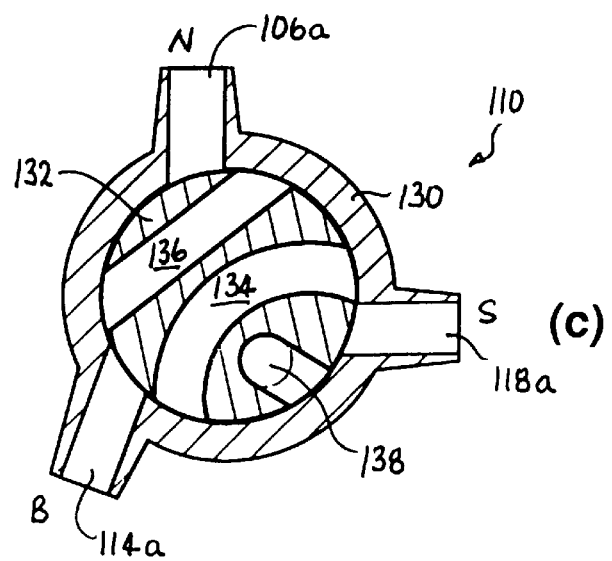

SAMPLING IN BLOOD COLLECTION

TECHNICAL FIELD

This invention relates to blood collection methods, and to apparatus for use therewith, in which venous blood is collected from blood donors and in which one or more blood samples are collected for analysis.

BACKGROUND OF THE INVENTION

It is imperative that the taking of samples during donation is done in such a way that contamination of the collected blood cannot occur through the process of sample collection. This rules out the use of tubular sampling ports and their associated vacuum phials, the use of pierceable or pre-slit septum ports, and the use of hypodermic needles to draw off samples from the blood line during donation, it being thereby possible for bacteria to be introduced into the blood flowing to the collection bag. Accordingly, it is standard practice to take samples after the desired amount of blood has been collected and after the line to the collection bags has been sealed. Samples can then be taken, using sampling ports, piercing the blood-line with a sampling needle or by dripping blood into open collection phials at any point between the IV needle (that is still in the donor's vein) and the point at which the line has been sealed.

Examples of known blood sampling methods in blood collection procedures are provided in the disclosure of U.S. Pat. No. 4,786,286 by Baxter International Inc. This publication, and that of WO 94/12093 also by Baxter, further disclose the use of in-line containers of various designs for blood sample collection after blood collection has been completed. In WO 90/12606, Baxter discloses the use of pre-slit septum ports for blood sampling during infusion techniques (but not during blood donation procedures). Other in-line sampling ports are disclosed by Spacelabs Inc in European patent publication No. 0 376 168.

Despite careful precautions to avoid contamination in blood collection procedures, a small percentage of blood packs become contaminated with bacteria. It is becoming recognised that, despite the use of topical disinfectants prior to puncture, contamination can occur by the inclusion of bacteria from the skin of the donor at the puncture site. The literature suggests that, in rare cases, a hollow vena-puncture needle can cut a 'plug' of skin from the donor's arm and that this plug may be carried into the collection bag along with the blood. It is postulated that the thickness of the plug is sufficient to protect bacteria within or just below the epidermis from the effects of the topical bactericide so that contamination of a blood pack can occur.

Besides not being wholly effective in preventing blood-pack contamination, the sampling procedures indicated above extend the duration of the collection procedure and the period during which the IV needle is in place in the patient's arm. This is because sample collection must be effected after the full unit of blood has been collected and the blood line has been sealed.

U.S. Pat. No. 3,654,924 to Wilson et al. teaches the use of a flow-through sample pouch formed around a portion of the blood line that includes a frangible connection so that, if a sample is required, the connection can be broken and blood allowed to flow into the sample pouch. U.S. Pat. No. 5,167,656 to Lynn also teaches the use of a flow-through sample-pouch but omits the use of the frangible connection in the blood line. Lynn's pouch fills with blood as blood flows to the bag-set and, after a unit of blood has been collected in the set, the line up-stream and down-stream from the pouch is sealed and the IV needle is withdrawn. Samples of blood may then be taken from the pouch. The use of such flow through pouches has the advantage that the procedure is shorter for the donor because samples can be taken from the pouch after the needle is removed from the donor's arm. However, the procedure is not significantly shortened from the standpoint of the phlebotomist who must still wait until collection is finished and the blood line has been sealed before taking samples. More importantly, it is highly likely that any skin plug in the initial flow of blood will be carried through the sample pouch and into the collection bag.

U.S. Pat. No. 4,056,101 to Geissler discloses the use of an in-line trap which is set to collect the first few millilitres (ml) of blood drawn from a donor. It is manually operable by pulling on the blood line to cause the remainder of blood flowing from the donor to pass to the bag-set. Its stated purpose is to capture tissue thromboplastin generated by the trauma of vein penetration. However, the device is not fool-proof. If the phlebotomist pulls on the blood line too early, the tissue thromboplastin will flow to the collection bag; if the blood line is not pulled sufficiently firmly to close the trap, the blood in the trap will mix with blood flowing to the collection bag. Moreover, since operation of this device depends upon a sliding joint between the blood-line in the body of the trap, it is not a closed system. It is possible that bacteria could find their way into the trap, and for blood to be transferred out of the trap, through the sliding joint.

Though Geissler makes no comment regarding the potential danger of contamination via a skin-plug, the trap of U.S. Pat. No. 4,506,101 will not offer a certain safeguard against this danger. First, as noted above, it is not fool-proof in that blood in the trap can mix with blood flowing to the bag-set if the trap is not operated correctly. Second, even if the trap is operated correctly, it is quite possible that a skin plug contained in the first few milliliters of blood will flow straight into the open end of the blood line which is directly opposite the inlet to the trap. Moreover, Geissler's trap is of no value in providing blood samples because there is no way of accessing the blood collected by the trap, nor was that intended as the volume of the trap is far too small to provide the samples normally required from each donor (30 to 40 ml).

In Japanese patent application No. 09028265 (Publication No. 10211274), Terumo Corp teaches the use of a first in-line frangible seal in the blood line between the IV needle and the blood bag and a second in a branch sample line connected to the blood line upstream of the first connector. Each seal blocks its respective line until it is broken by external manipulation of the line. After the IV needle is inserted in the donor, the second seal is broken to allow blood to flow into the sample line for removal via a sample port connected to the sample line. The first seal is then broken to permit flow of blood to the collection bags. While this procedure is intended to ensure that the initial blood flow is directed to the sample tube, portion of that flow (perhaps containing the skin plug) will fill the blood line upstream of its seal and then be conveyed to the blood pack after the first seal is broken. If samples are taken during blood collection, the system will be opened; if samples are taken after collection has been completed and the blood line sealed, the procedure will be prolonged (as with the conventional procedure).

Finally, it will be appreciated that, whilst the present invention is concerned with blood sampling in association with the collection of blood from donors, systems are known for collecting samples of arterial blood during medical procedures that employ indwelling catheters for infusing saline solutions or medication and that attempt to minimise blood spillage or waste during sample collection. For example, U.S. Pat. No. 5,772,608 to Dhas discloses a system for infusing medication into the artery of a patient that uses manually operable valves to employ the patient's arterial blood pressure to flush the medication from the line into a waste bag before blood samples are taken from the line via a normal sampling port. The issue of contamination of collected blood by skin plugs and is the like are clearly not relevant in such procedures.

BRIEF SUMMARY OF THE INVENTION

The present invention involves the use of a multi-port/multi-position valve in the blood line from the needle to the collection bag that can be operated to first connect the needle line to a branch line at the start of the blood collection procedure and then connect the needle line to the bag line for blood collection. The arrangement is preferably such as to ensure that any skin plug is diverted with the initial blood flow to the branch line. Preferably, the branch line itself comprises—or is connected to—a sealed container or pouch for holding sample blood. The branch line may therefore be referred to below as the 'sample line'.

The multi-port valve preferably seals-off the bag-line while the sample blood is collected and seals off the sample line while main blood collection takes place. This ensures that any skin plug and thromboplastin is captured by the sample container and allows samples for analysis to be drawn from the sample container (using conventional techniques) while blood collection takes place. Thus, the likelihood of pack contamination is reduced and the time taken for the procedure is shortened.

As between 30 and 60 mls of blood is normally required for a normal set of samples during blood collection from a single donor, it will be seen that there is plenty of initial blood flow to carry any skin plug into the sample container and that, furthermore, there is no possibility that the skin plug can find its way from the sample line into the blood line to the bag-set.

The valve may be fitted with safety means to ensure that (i) the initial blood flow cannot be inadvertently transferred to the bag line, (ii) the bag-line and the sample line can never be interconnected and/or (iii) neither the bag line nor the sample line can be reconnected to the needle line after blood flow to the bag set has been terminated by use of the valve.

More than one sample container may be employed and clamps or similar devices may be used to direct sample blood flow to each in turn until sufficient sample blood has been collected. This allows the initial blood flow (containing any skin plug) to wash any anticoagulant or saline fill in the needle and sample lines into the first sample container so that blood directed to subsequent sample containers will be free of such diluents.

If the sample container(s) is rigid or semi-rigid, some means of allowing air therein to escape as it fills will be required. Filtered vents with automatic shut-offs for this purpose are well known in the art. Preferably, however, the sample container is a small flexible lay-flat pouch substantially free of air, (not unlike the bags of the collection set) which can expand as blood flows into it. Such a sample pouch can be divided into a plurality of interconnected sub-pouches that are collectively or individually capable of being removed from the sample line for later access. Preferably, the volume of blood taken for samples in this way should be controllable by the phlebotomist in a simple manner; for example, by folding over and dipping the pouch or closing off one or more of the sub-pouches or containers. Most preferably, the volume of blood collected for samples may be controlled by the use of the valve operated manually by the phlebotomist, though the use of such a valve may be in addition to control of the volume of the sample collection container(s).

For convenience, the sample container will be referred to below as a 'pouch' though it will be appreciated from the above that such a container is not the only one envisaged.

The valve means may be a rotary or linear valve, or a combined rotary and linear valve. It is preferably such that it can only be operated in one direction so that (i) the sample pouch cannot be re-connected to the blood line after flow to the collection bag has been closed off, and (ii) the bag set cannot be reconnected to the blood line after the valve has been placed in the 'off position' at the end of blood collection. However, it is also desirable (but not essential) for the valve to be arranged to allow anticoagulant to be fed to the bag set during manufacture so that the valve can be fitted to the blood lines before filling and, of course, prior to sterilisation.

The valve means may incorporate a sample port for the connection of a conventional sampling syringe, vacuum phial or other sampling device, thereby saving the need for a Y-connector in the line to the sample pouch. For example, the port may comprise a pre-slit septum device of the type disclosed in WO 90/12606 by Baxter International Inc. The valve actuator means and the sample port may be fixed together so that the sample port may be used to manipulate the valve.

The valve may be anchored to the arm of the donor by a suitable strap or the like. Conveniently, this may be a wrist strap and the valve can be attached to the strap by Velcro or the like. The immobilisation of the blood line in this way is an added advantage for the comfort of the donor and may avoid the need for the use of a conventional adhesive strip for this purpose. The strap also ensures that the movement of the sample pouch necessary for operation of the sample port and vacuum phials cannot affect the needle line or the blood collection line.

As already indicated, the valve may provide a connector for the sample port or a tube could be led from the valve for connection to the sample port. Alternatively, a tube having a sample port (or a connector for such a port) on one end may be connected by its other end to the bottom of the sample pouch. In that case, it is preferable to attach the sample port itself to the top of the sample pouch so that it does not hang down and is located at a convenient angle for use.

BRIEF DESCRIPTION OF THE SEVERAL VIEWS OF THE DRAWINGS

Having broadly portrayed the nature of the present invention, exemplary embodiments will now be described with reference to the accompanying drawings, in which:

FIG. 2 is a series of three diagrams, (a), (b) and (c) showing the valve of FIG. 1 in horizontal section in respective operational positions.

DETAILED DESCRIPTION OF THE INVENTION

Figure 1:
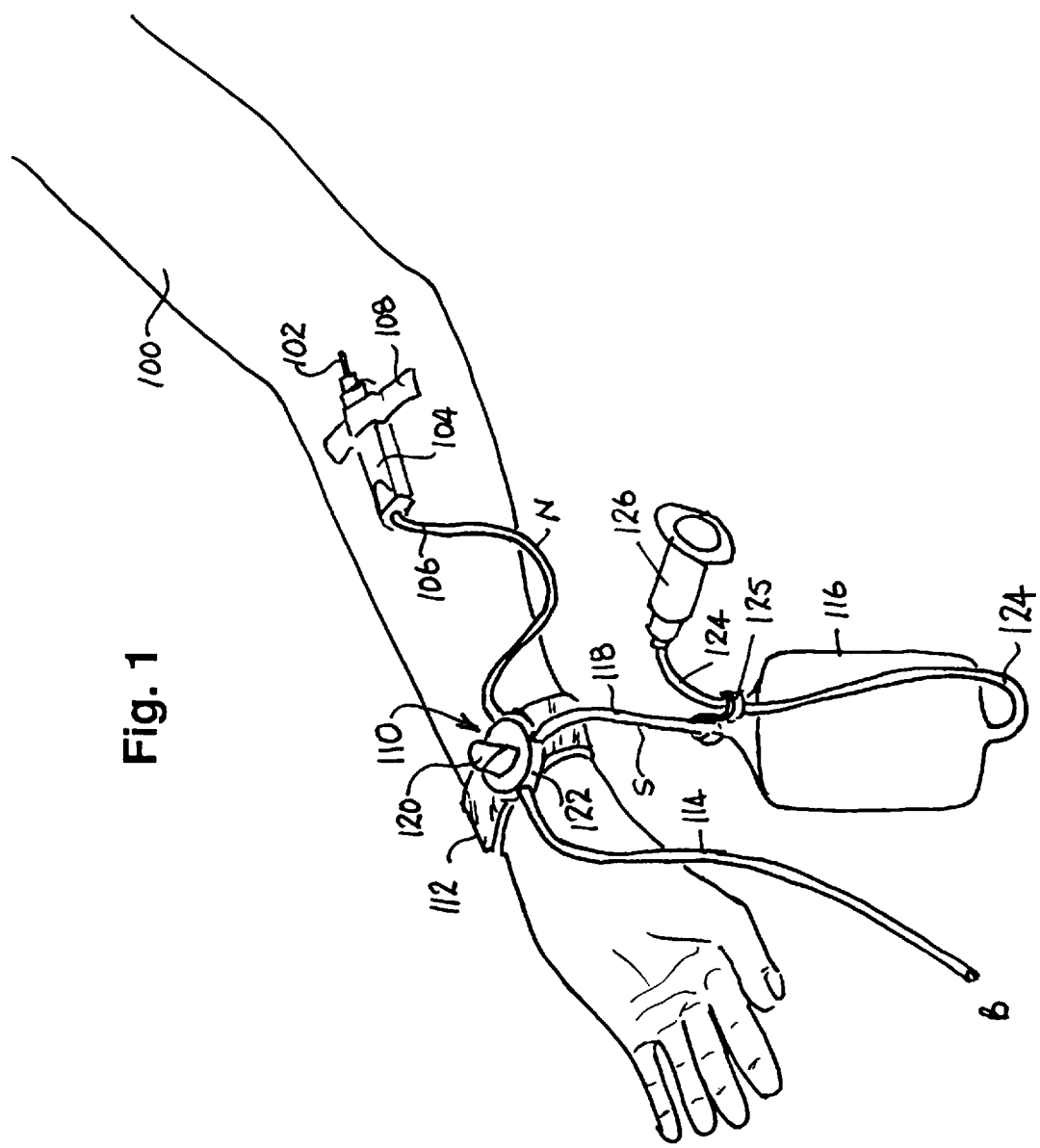
FIG. 1 illustrates a blood collection set formed in accordance with the first example of the present invention wherein a rotary multi-port valve on a wrist-strap is employed.

Referring particularly to FIG. 1, the first embodiment of the invention is shown in position on a donor's arm 100 with the needle 102 in place in a vein and blood being collected, needle 102 being partially located within a needle guard 104 into which it is withdrawn when it is pulled from the donor's vein by the needle tube or line 106. Needle guard 104 is affixed to arm 100 by an adhesive tape 108.

This embodiment employs a multi-port rotary valve 110 that is fixed to a wrists trap 112 and is arranged to switch blood flowing from needle tube or line 106 to either the bag tube or line 114 that is connected to the bag set (not shown) or to a sample pouch 116 via a sample tube or line 118. Valve 110 is manually operated by turning the arrow-shaped actuator knob 120, the body 122 of the valve being temporarily attached to the donor's arm 100 by wrist strap 112. A tube 124 extends upwardly from the bottom of sample pouch 116 and is attached by a clip or hook 125 to sample line 118, the upper end of tube 124 being connected to the sheathed needle (not shown) of a conventional sample port 126. [In this and succeeding examples, the needle line, bag line and sample line are additionally indicated by the letters N, B and S respectively].

At the start of blood collection (ie, when needle is being inserted into arm 100), valve 110 is set (as shown) so that blood from needle line 106 is directed into sample line 118 and no blood flows into bag line 114. After sufficient sample blood has been collected in pouch 116, valve actuator 120 is turned to direct blood flow from needle line 106 to blood line 114 for collection in the bag set (not Shown). In that position, there is no connection between needle line 106 and sample line 118. Accordingly, while collection is taking place, samples can be taken from pouch 116 by the use of sample port 126 and vacuum phials (not shown) in the normal manner.

The operation of multi-port rotary valve 110 is illustrated in the three positions—(a), (b) and (c)—of the valve shown in FIG. 2. The body 122 of valve 110 comprises a stator ring 130 that has an inlet 106a for connection to needle line 106, a first outlet 118a for connection to sample line 118 and a second outlet 114a for connection to bag line 114. The inlet and outlets open to or from a central chamber in ring 130 within which an cylindrical actuator 132 is located for rotary (or, more precisely, arcuate) movement therein. Actuator has a curved channel 134 and a straight channel 136 extending from one side thereof to the other, the channels separate and not connected. In position (a), blood from needle line inlet 106a is directed to sample line outlet 118a via curved channel 134 while bag line outlet 11 4a is sealed off. In position (b), blood from needle line inlet 106a is directed to bag line outlet 114a via straight channel 136 and sample line outlet 118a is sealed off. In position (c), inlet 106a and both outlets 114a and 118a are sealed off or closed preparatory to disposal of the unit. It will also be seen that there is an intermediate position between positions (a) and (b) in which the inlet and both outlets are closed.

Valve 110 allows for an optional sampling port 138 in the top of rotor/actuator 132. This may be a self-sealing port that will accept the tapered spigot of a standard syringe or sampling port. If the sampling port includes a raised spigot, it can be used to rotate the rotor 132 of valve 110. It will be seen that port 138 is only connected to sample line outlet 118a (and, thus, to sample pouch 116) when actuator 132 is in position (b), but this allows the samples to be drawn off with complete safety while blood is flowing to the bag set. Normally, it will be more convenient to sample via sample pouch line 124 and sample port 126 as described with reference to FIG. 1. In that case, since there is no need for port 138 in valve 110, port 138 can be omitted and channel 134 can be straight like channel 136, if desired.

During manufacture of the blood collection assembly, it may be convenient to attach valve 110 to the various connecting lines and the sample pouch before anticoagulant is introduced into the bag set and the assembly is sterilised. In that case, valve 110 is set so that its rotor is as shown in (b) so that anticoagulant can be introduced into the bag set via the needle line 114 and bag line 114. Normally, anticoagulant is not required in the sample pouch 116. For foolproof operation of valve 110, it is desirable that (i) rotor 132 can only turn dockwise and (ii) it cannot be turned beyond position (c) of FIG. 2. One way of achieving this will be described with reference to FIGS. 3 and 4.

Figure 3:
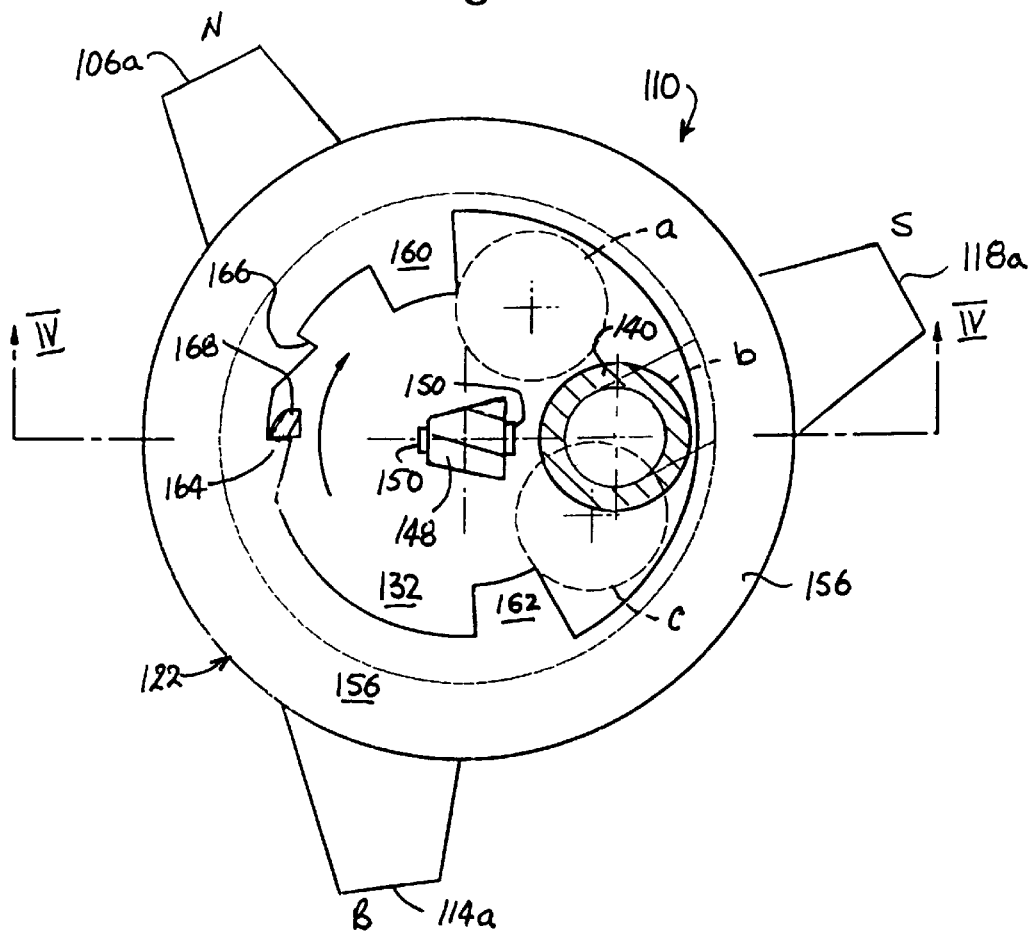
FIG. 3 is a plan view of the valve of FIG. 1 taken on section plane III—III of FIG. 4.
Figure 4:
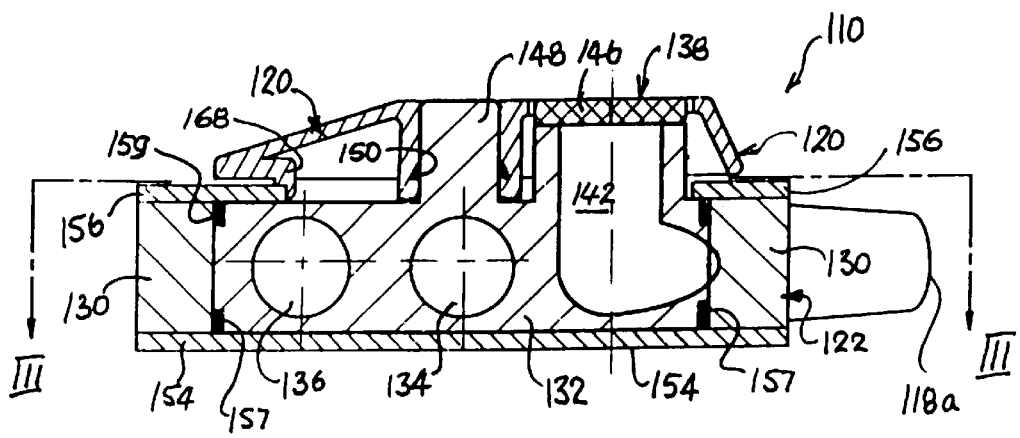
FIG. 4 is a sectional elevation of the valve of FIG. 1 taken on section line IV—IV of FIG. 3 assuming that the actuator knob of the valve is in place.

As depicted in FIGS. 3 and 4, valve 110 is shown in position (b) of FIG. 2 where sample port 138 is in communication with sample-line outlet 118a. In this example, sampling port 138 comprises a short hollow spigot 140 that stands up from the upper surface of rotor 132, has a bore 142 that connects with outlet 118a and has its upper end sealed by a pre-split septum 146 of a type known in the art. Rotor/actuator 132 has a central integral upstanding shaft 148 of trapezoidal section that takes knob 120 (FIG. 4), shaft 148 having external detents 150 so that knob 120 is a snap-fit thereon. As previously noted, body comprises a ring-like moulding 130 that includes inlet 106a and outlets 114a and 118a and that encompasses rotor 132, which is retained between a disc-like bottom plate 154 and a ring-like top catch-plate 156. Rotor 132 is provided with a pair of peripheral ring seals 157 and 159 in a manner known in the art.

The inner periphery 158 of catch-plate 156 is formed with a pair of opposed inwardly projecting stops 160 and 162 that limit the rotary movement of rotor 132 by engaging spigot 140 of port 138. When rotor/actuator 132 is in position (a) of FIG. 2, the base of spigot 140 (indicated by dotted-line circle a in FIG. 3) abuts stop 160, and, when rotor/actuator 132 is in position (c) of FIG. 2, spigot 140 abuts stop 162 (as indicated by circle c). As already noted, rotor 132 is shown in FIGS. 3 and 4 in position (b) of FIG. 2, this being indicated by the letter b applied to spigot 140 in FIG. 3.

The inner periphery of catch-plate 156 is also formed with a pair of inwardly projecting ratchet teeth 164 and 166, tooth 164 being diametrically opposite spigot 140 when in position (b) of FIG. 2 and tooth 164 being diametrically opposite spigot 140 when in position (c) of FIG. 2. The teeth are engaged by a resiliently mounted pawl 168 formed integrally with knob 120. In FIG. 3, with rotor 132 in position (b), pawl 168 is shown engaging tooth 164, preventing return of the rotor to position (a). When rotor 132 is in position (c), pawl 168 engages tooth 166, preventing return of rotor 132 to position (b). In fact, rotor 132 will be locked in position (c) since it cannot be advanced clockwise any further because of abutment of spigot 140 with stop 162.

This arrangement allows valve 110 to be assembled at manufacture with knob 120 fitted to shaft 148 but not pressed down to engage detents 150. In this position of knob 120, pawl 164 is located above the level of catch-plate 156 so that it cannot engage either of teeth 164 or 166, allowing rotor 132 to be turned clockwise or anticlockwise between positions (a), (b) and (c). Thus, after tubes 106, 114, and 118 have been fitted, valve 110 can be set in position (b) and anticoagulant fed to the bag set via needle line 106, passage 136 and bag line 114 and the entire assembly can be sterilized. After sterilization, rotor 132 can be turned anticlockwise to position (a). Actuator knob 120 can then be pressed firmly downwards to engage indents 150 and bring pawl 168 into the same plane as catch plate 156. Thereafter, the assembly can be used as described with reference to FIGS. 1 and 2.

The second example of a multi-port valve suitable for use in the system of the invention is illustrated in longitudinal section in FIGS. 5A to 5D. This valve 200 has a T-shape body 202 having axially aligned spigots 204 and 206 onto which needle line 106 and bag line 114 are respectively attached. An actuator 208 is mounted for sliding and rotational movement within body 202 and is fitted with a knob 210 on its upper end, its lower end being formed as a spigot 212 to take sample line 118. Actuator 208 has an upper cross-bore 214 and a lower axial bore 216 that communicates with a side opening 218. Optionally, body 202 can have a rear port 220 (shown in broken lines) that is fitted with a septum or is otherwise adapted for connection to a syringe or sampling port. Actuator 208 has four inset-moulded ring seals (shown shaded but not assigned reference numerals for the sake of clarity), seals being located above and below cross-port 214 and seals being located above and below side port 218.

Figure 5A:
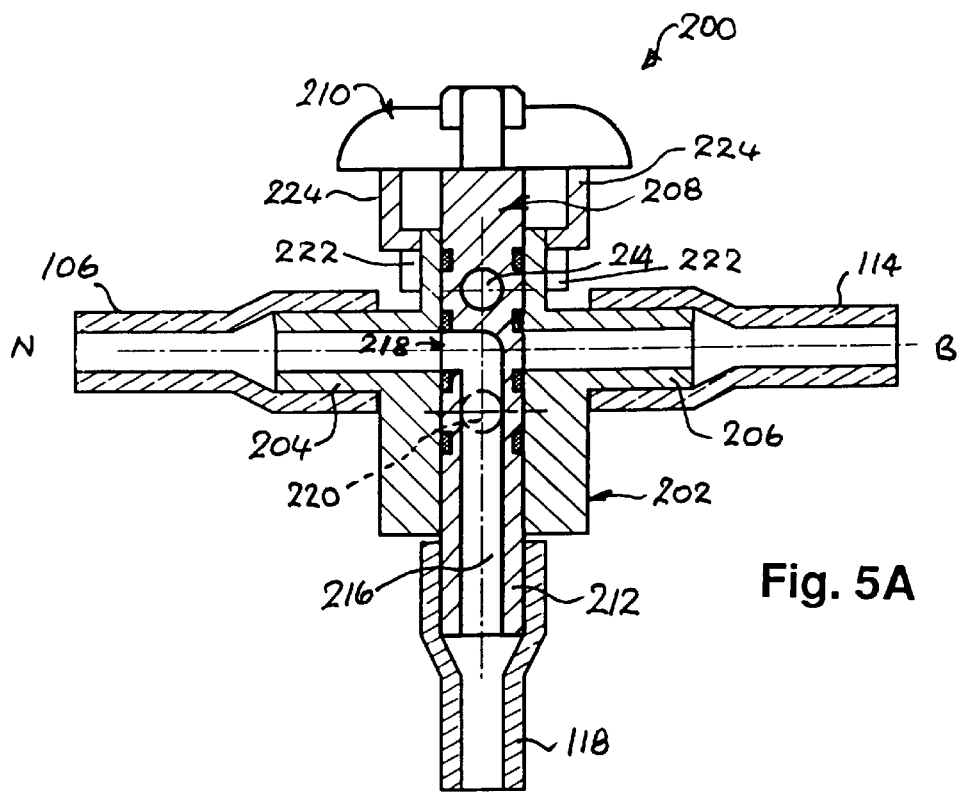
FIGS. 5A to 5D are sectional elevations of the multi-port valve of the second example, each Figure showing a different operational position of the valve.
Figure 5B:
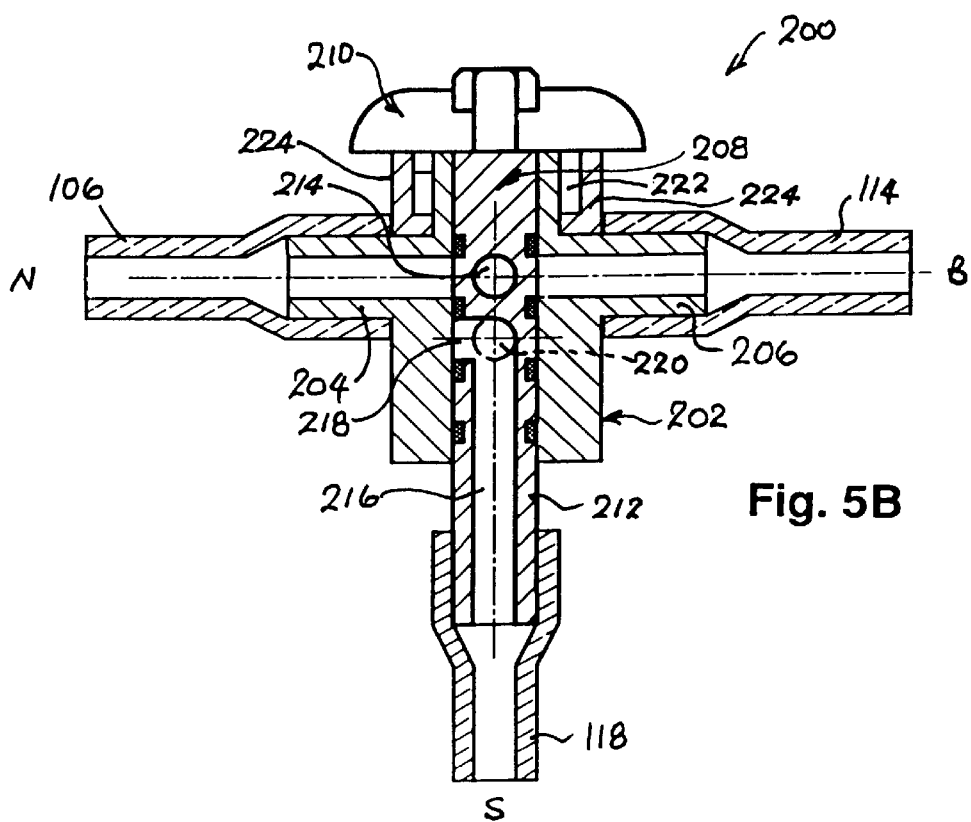
Figure 5C:
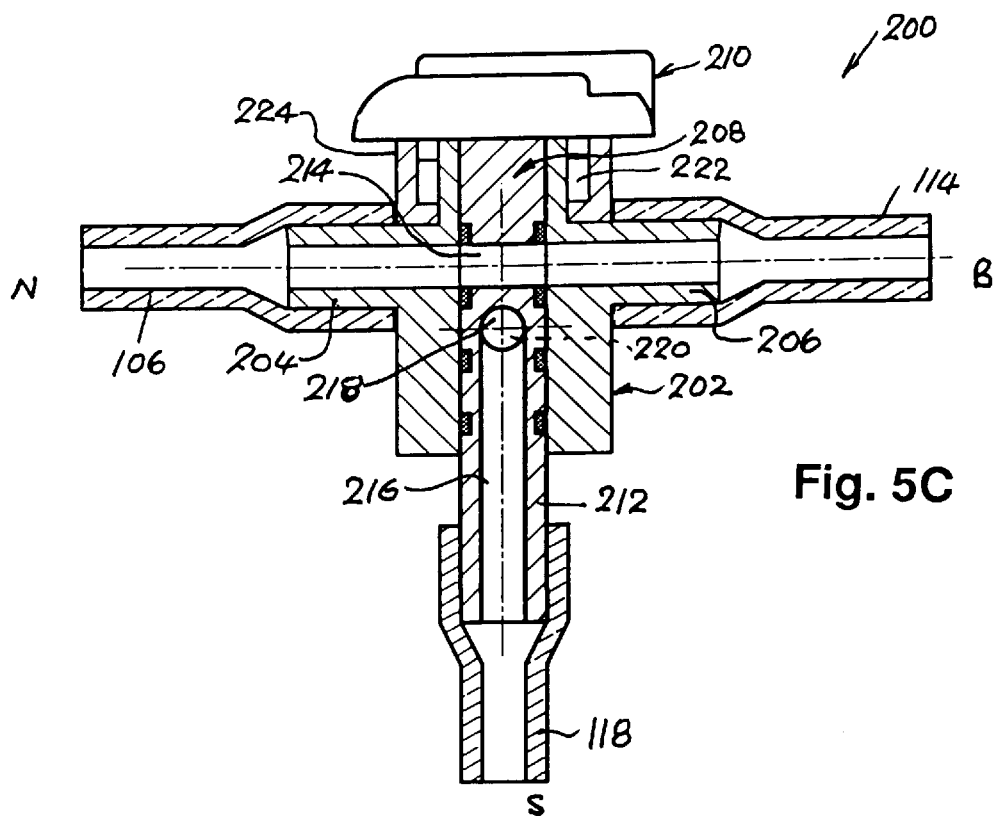
Figure 5D:
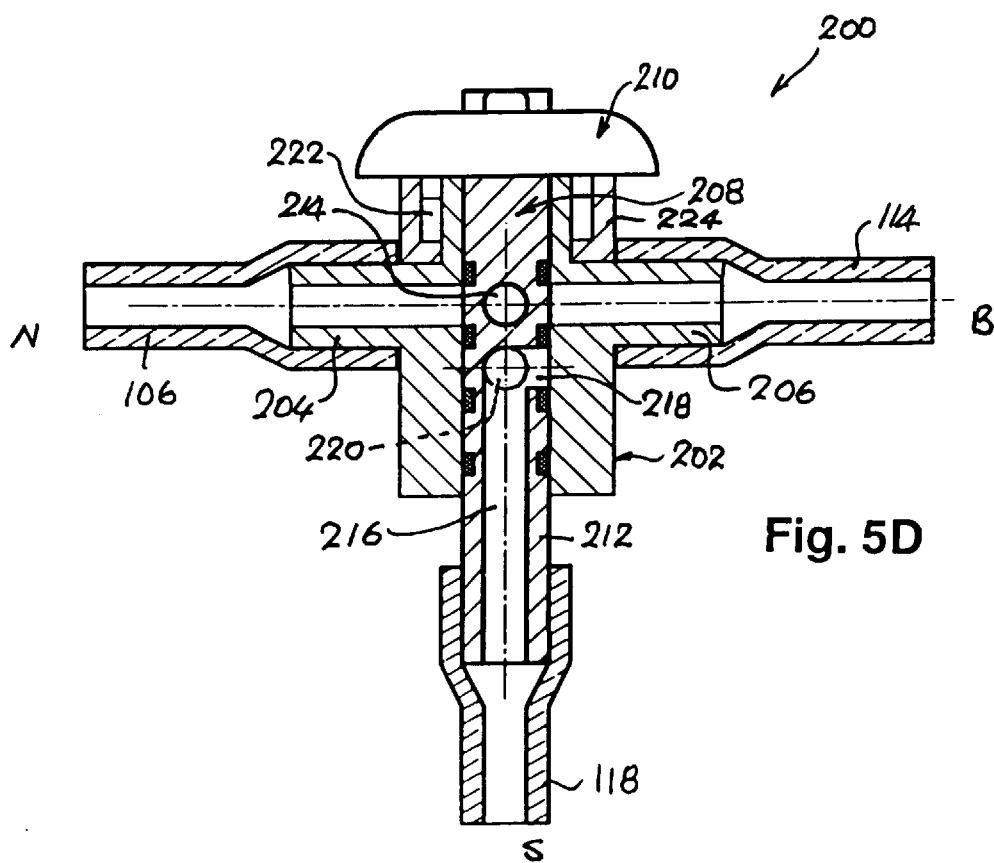

In the position shown in FIG. 5A, valve actuator 208 is set to channel blood from needle line 106 direct to the sample tube 118 via outlet spigot 212 and to close-off outlet spigot 206 to bag line 114. After sufficient blood for samples has been taken, valve member 208 is pressed down to bring cross-bore 214 to the same level as spigots 204 and 206, closing off port 218 and stopping the flow of blood from needle line 106 while keeping bag line 114 closed. This position is shown in FIG. 5B. Actuator 208 is then turned through 90 degrees using knob 210 to align cross bore 214 with inlet spigot 204 and outlet spigot 206 so that blood can flow from needle line 106 to bag line 114, as shown in FIG. 5C. In this position of actuator 208, side port 218 is aligned with rear sample port 220 of body 202 so that samples can be drawn off via that port while blood collection is under way without 'opening' the blood line (ie, needle line 106 and bag line 114 of FIG. 1) to contamination via sample line 118 or rear sample port 220 in body 202. Finally, after sufficient blood has been collected, valve member 208 is turned through a further 90 degrees to close off the flow of blood to the bag set and so as to close off sample port 220. This final position is shown in FIG. 5D.

The top of valve body 202 is fitted with slots 222 that are engaged by L-shape members 224 depending from the underside of knob 210. This prevents actuator 208 from being rotated until it has been pushed down. A ratchet mechanism (not shown) then constrains actuator 208 to only turn clockwise. Stop means (also not shown) prevent member 208 from being turned beyond the position of FIG. 5D.

Figure 6:
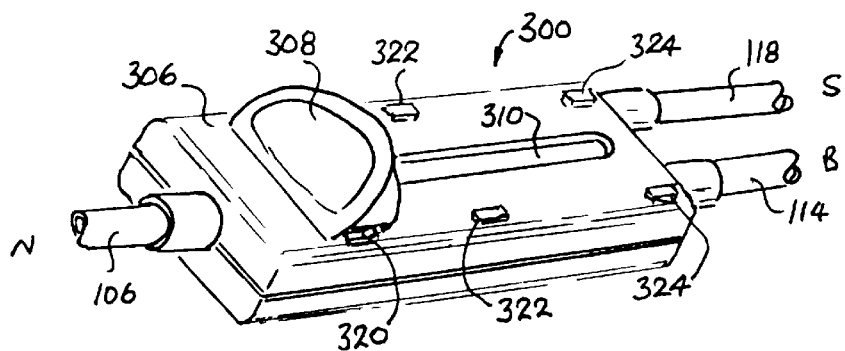
FIG. 6 is a perspective view of the third example of a multi-port valve formed in accordance with the present invention.
Figure 8:
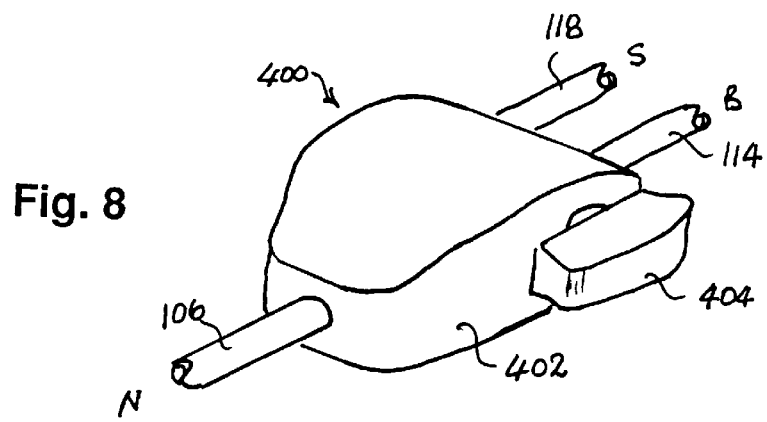
FIG. 8 is a perspective view of the fourth example of a multi-port valve formed in accordance with the present invention.
Figure 7:
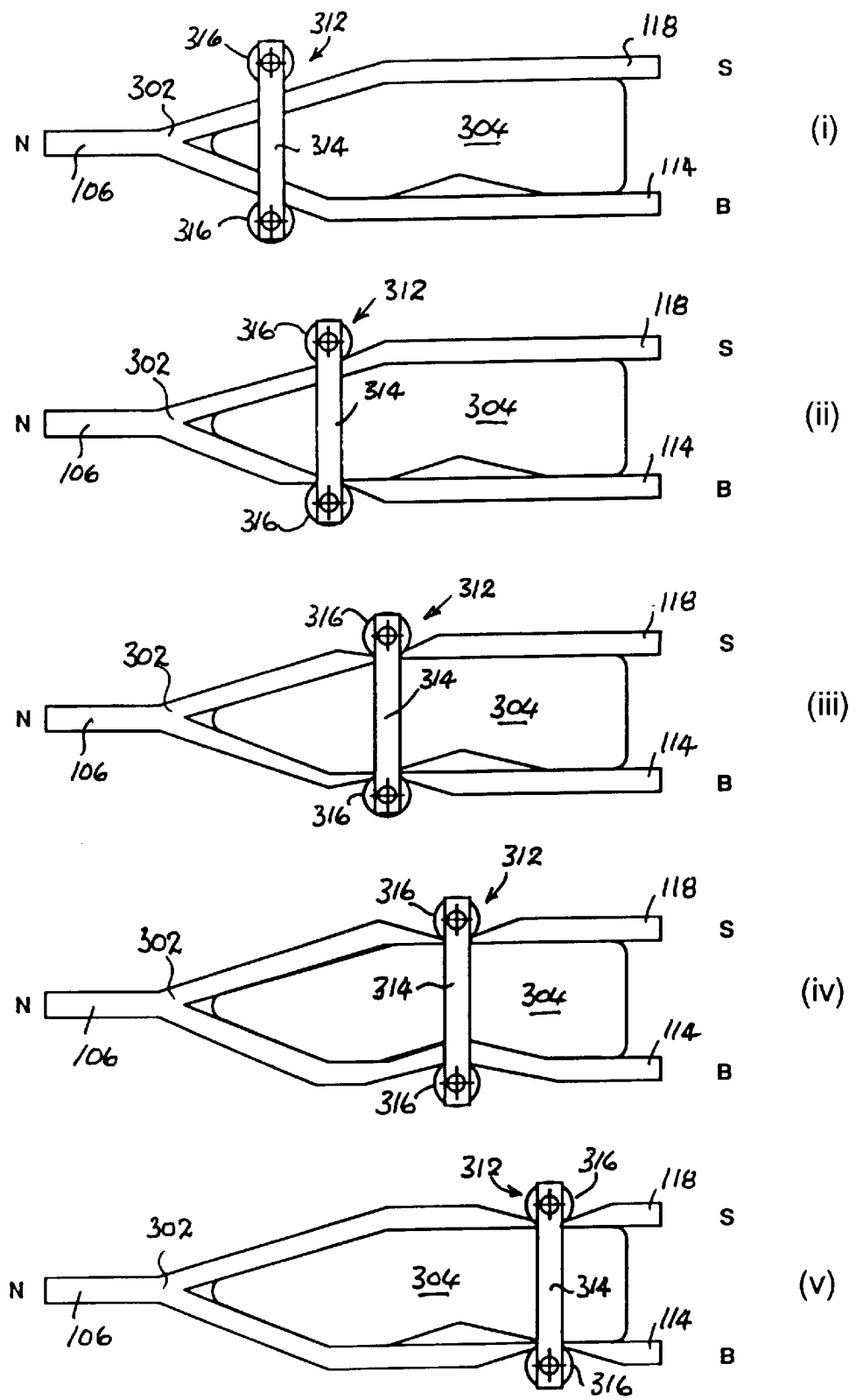
FIG. 7 is a series of diagrams, identified as (i) to (v) showing the operation of the valve of FIG. 6 in respective operational positions.

The third example of a multi-port/multi-position valve suited for use in the system of the invention is shown in FIGS. 6 and 7. This valve is a linear slide-valve 300 into which needle line 106 is led and from which bag line 114 and sample line 118 emerge, needle line 106 having a Y-junction 302 from which lines 114 and 118 emerge and are led over opposite edges of a central mandrel or anvil 304 (see FIG. 7) located in the casing 306 of valve 300. In this valve, needle line 106 can be regarded as the inlet, the point of exit of sample line 118 can be regarded as the first outlet and the point of exit of the bag line 114 can be regarded as the second outlet. The valve is operated by an actuator knob 308 arranged for sliding movement guided by a longitudinal slot 310. Knob 308 is connected to a sliding actuator 312 (FIG. 7) that is located within casing 306 and that comprises a bar 314 with a roller 316 mounted at each end. The arrangement is such that bar 314 is moved longitudinally by knob 308 so that rollers 316 ride on tubes 114 and 118 to compress them against mandrel 304, according to the shape of the mandrel.

FIG. 7 diagrammatically indicates the function of valve 300 in five stages (i) to (iv). In stage (i), actuator 312 is to the far left and all lines are open so that they can be sterilised. Before the needle is inserted into the donor's vein, actuator 312 is moved to the position shown in stage (ii), where the bag line 114 is pinched closed by the lower roller against mandrel 304 but the sample line 118 remains open. The needle is then inserted and blood from needle line 106 flows through sample line 118 to sample pouch 116. After sufficient sample blood has been collected, actuator 312 is moved to the position shown in stage (iii) in which both bag line 114 and sample line 118 are blocked. Moving actuator 312 further to the right to position (iv) results in the release of bag line 114 (because of the shape of mandrel 304) so that blood flows through bag line 114 to the collection bags. While collection is proceeding, samples can be drawn off pouch 116 using sample port 126 (FIG. 1). After sufficient blood has been collected, actuator 312 is moved to the extreme right as shown in stage (v) so that both bag line 114 and sample line 118 are again closed. The needle is withdrawn, the bag line crimped and severed and the needle, tube and valve assembly are disposed of in a suitable manner.

To prevent actuator 312 being moved in the reverse direction (ie, from right to left in FIGS. 6 and 7) the top of valve casing 306 is provided with three pairs of protrusions 320, 322 and 324 along its sides that are engaged by knob 308 in a ratchet-like manner. The protrusions are located on the casing so that: when knob 308 is moved right to engage protrusions 320, actuator 312 is located in position (ii) [FIG. 7] and blood is directed to the sample line 118 and pouch 116 [FIG. 1]; when knob 308 is moved right to engage protrusions 322, actuator 312 is located in position (iv) and blood flows to bag line 114; when knob 308 is moved to the extreme right and engages protrusions 324, actuator 312 is in position (v) and both lines 114 and 118 are sealed.

The fourth example of a multi-port or multi-position valve suited to use in the system of the invention is shown in FIGS.

Figure 9:
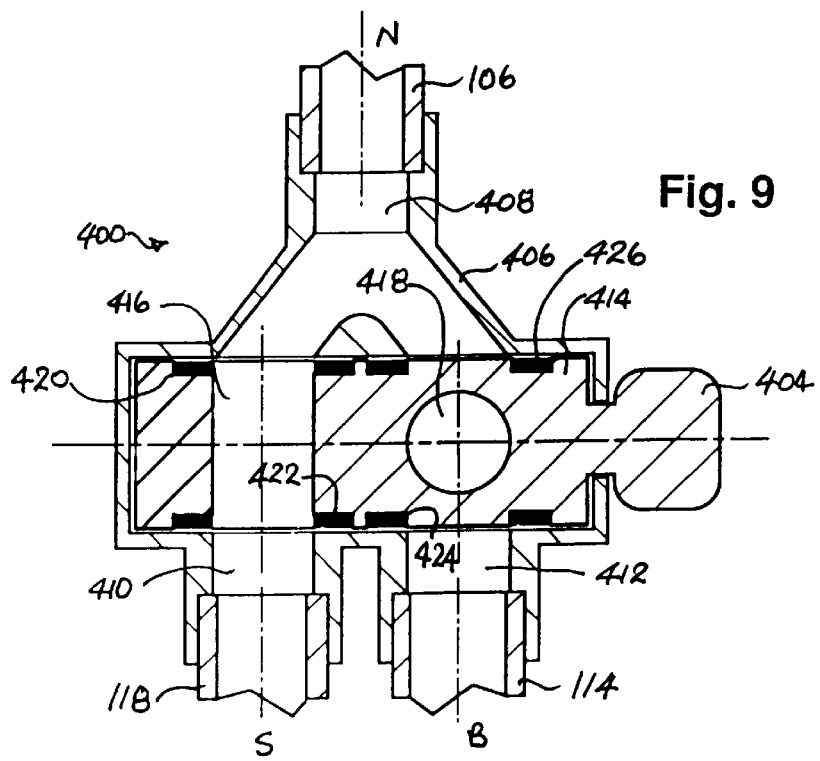
FIG. 9 is a sectional plan view of the body of the valve of FIG. 8.

8 and 9. The valve 400 has an external casing 402 into which is led needle line 106 and from which bag line 114 and sample line 118 emerge. [Casing 402 is not shown in FIG. 9.] A rotating actuator knob 404 operates valve 400, turning about an axis that lies transverse to the blood lines. A bifurcated valve body 406 (FIG. 9) is located in casing 402 and has an inlet 408 into which needle line 106 is secured, a first outlet 410 into which sample line 118 is secured and a second port 412 into which bag line 114 is secured. A barrel-like actuator 414 fits within a cylindrical recess in body 406 between the inlet and outlets and is formed integrally with or attached to actuator knob 404 for rotation thereby. Actuator 414 has a first cross bore 416 that can be aligned with first outlet 410 upon rotation of the actuator casing 402 and a second cross bore 418 that can be similarly aligned with second outlet 412, bores 416 and 418 being spaced apart and oriented at right angles to one another. A first pair of ring seals 420 and 422 are arranged one on each side of bore 416 and a second pair of ring seals 424 and 426 are arranged one on either side of bore 418 to ensure that blood cannot leak between the bores around actuator barrel 414.

Depending upon the orientation of actuator 414, bore 416 can be aligned with first outlet 410, bore 418 can be aligned with second outlet 412, and between those positions, both ends of both bores can be closed by body 406. Thus, at the start of bleeding, actuator 414 is turned by knob 404 to bring bore 416 into line with outlet 410 to connect the needle line 106 with the sample line 118. Then, by further turning actuator 414, bore 416 is turned so that this connection is broken and flow to sample line 118 is stopped. Further rotation of actuator 414 then brings bore 418 into line with second outlet 412 to connect needle line 106 with bag line 114, while still cutting off flow to sample line 118. This allows blood collection to proceed while samples are taken from sample pouch 116 as previously described. Finally, further rotation of actuator 414 results in blood flow to bag line 114 being cut off while still stopping all flow to the sample line 118. The needle may then be withdrawn, the bag lines severed and the valve assembly disposed of.

Figure 10:
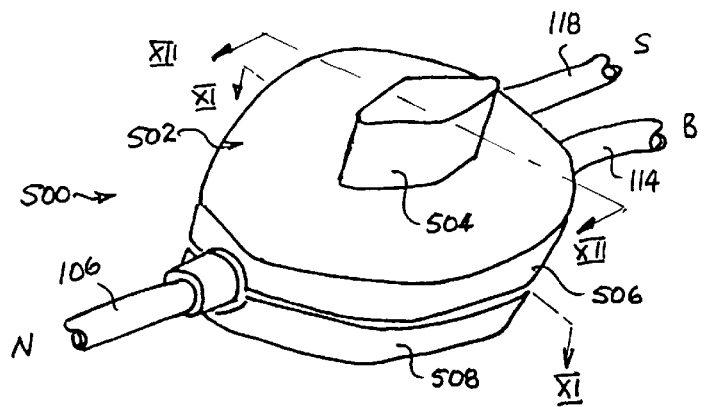
FIG. 10 is a perspective view of the fifth example of a multi-port valve formed in accordance with the invention.
Figure 11:
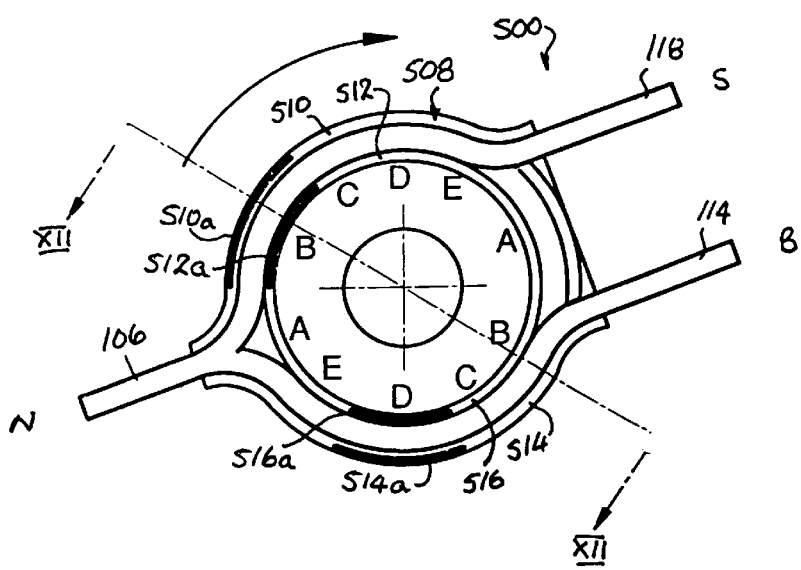
FIG. 11 is a plan view of the bottom half the valve of FIG. 10 taken on plane XI—XI of FIG. 10.

The fifth example of a multi-port or multi-position valve suited for use in the system of the invention is shown at 500 in FIGS. 10 and 11 and, as in the previous example. Includes a casing 502 into which needle line 106 enters and divides in to sample line 118 and bag line 114 that emerge from the casing. As with the third example, it is appropriate to regard the needle line near the junction of the sample and bag lines as the inlet to the valve, to regard the point at which the sample line emerges from the casing as the first outlet and to regard the point at which the bag line emerges from the casing as the second outlet of the valve. An actuator knob 504 emerges from the centre of the upper half 506 of casing 502. It can be turned to effect the functions of the valve. The bottom half 508 of casing 502 is shown in FIG. 11 with the top half 506 removed. Tube 118 is fitted between a pair of arcuate channel walls 510 and 512 formed around one side on the upper surface of bottom half 508, while tube 114 is fitted between similar channel walls 514 and 516 on the other side of bottom 508. A circular ridge 510 forms the inner sides of the channels while part circular peripheral ridges 512 and 514 form the outsides of the respective channels. Portions of these walls (identified by the suffix a) rise higher than the rest from bottom half 508.

In this example, the actuator comprises a radially extending axle 518 pivoted at its centre to a shaft 519 on which knob 504 is fixed and by which it can be turned about the axis of shaft 519. Axle 518 carries an idling roller 520 on each end that can run on tube 118 and/or 114 and pinch them closed in their respective channels. While it is able to move up and down to a limited degree in shaft 519 because its pivot pin 522 is located in a slot 524, axle 518 is biased toward base 508 by a leaf spring 526. The force of spring 526 is taken by a flange 528 on the bottom of shaft 519 that engages a recess in the base of bottom half 508. and carrying a roller 520 at each end When halves 506 and 508of valve casing 502 are assembled, the axle and rollers are fully contained with the casing and are spring-loaded onto the bottom half 508 of the casing.

In an alternative arrangement, the rollers may be mounted directly to the upper half 506 of casing 500, which can rotate relative to the lower half 508, and the two halves of the casing may be spring-loaded together so as to bias the rollers onto the tubes 114 and 118. In that case, the rollers and the upper part of the casing would form the actuator means, allowing knob 504 to be omitted. Both versions of the valve 500 operate in the manner explained below.

Figure 12:
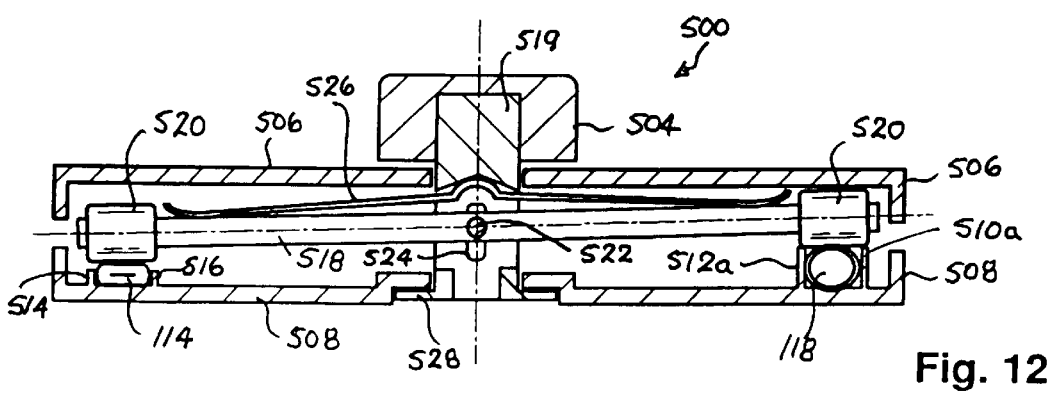
FIG. 12 is an enlarged cross section of the valve of FIGS. 10 and 11 taken on plane XII—XII of those FIGS.

The operation of valve 500 is conveniently explained by reference to the pairs of letters A to D of FIG. 11 that indicate a sequence of positions of the axle and/or rollers (not shown). The valve is shipped with the actuator rollers in position A—A supported on the bottom casing half 508 and not on tubes 114 and 118. In this position, anticoagulant can be fed to the bag-set and the whole assembly can be sterilised. When the valve is ready to use, the actuator rollers are moved to position B—B in which bag line 114 is pinched dosed by one roller but in which sample line 118 remains open because its roller is held up by the raised portions 510a and 512a of the channel walls between which tube 118 is confined. Note that this position of the valve is that shown in FIG. 12. After sufficient blood has been collected in the sample pouch 116, the rollers are moved through position C—C (in which both tubes are blocked) to position D—D in which the sample line 118 is blocked and bag line 114 remains open because its roller is held off the tube by ramps 514a and 516a. [As in the previous examples, samples can be drawn from sample pouch 116 while blood flows to the collection bag via line 114.] Finally at the end of the blood collection procedure, the rollers are moved to position E—E in which both tubes are again blocked. As in the other examples, it is preferable that some ratchet mechanism be employed to ensure that (i) the rollers cannot be moved in the anticlockwise direction (in FIG. 11) and (ii) they cannot be moved clockwise beyond position E—E.

While a number of examples have been described, it will be appreciated that many variations and alterations can be made thereto without departing from the scope of the invention as defined by the following claims.

It will also be appreciated that the first two examples are to be preferred over the others because they preclude the possibility that the skin plug might lodge in the bag line just after the Y-joint with the sample line, even though the bag-set tube is closed off further down stream. Nevertheless, all examples offer substantial advantages over the conventional collection procedures by reducing procedure time by allowing samples to be drawn during blood collection.

What is claimed is:

1. A blood collection method wherein blood is drawn from a donor via a needle line and is conveyed to a collection bag via a bag line, the method comprising the steps of:

moving an actuator in valve means connected between the needle line and the bag line to open a first connection causing initial blood flow to be directed from the needle line to a sample line while preventing access by blood in the needle line to the bag line, the sample line comprising or being connected to sample collection means, moving said actuator to close said first connection stopping said initial blood flow while continuing to prevent access to blood to the bag line, after a blood sample has been collected in said sample collection means, and moving said actuator to open a second connection between the needle line and the bag line to allow blood flow to the bag line while continuing to keep said first connection closed so as to prevent access by blood in the sample line to the needle line and to the bag line.

2. A method according to claim 1 including the further step of moving said actuator to close said second connection while continuing to keep said first connection closed, thereby preventing access by blood between the needle line, the bag line and the sample line, after blood has been collected in the collection bag.

3. A method according to claim 1 wherein said sample collection means comprises a sample pouch connected to the sample line, the method including the steps of:

allowing said initial blood flow through the sample line to continue until sufficient blood for at least one blood sample has been collected in said sample pouch for use in subsequent analysis, and drawing off said blood sample while said second connection is open, blood is flowing from the needle line to the bag line and the first connection between the needle line and the sample line is closed.

4. A method according to claim 1 including the step of securing the valve means to the arm of the donor at the outset of the blood collection procedure and removing said valve means from the arm of the donor at the end of the procedure.

5. Apparatus suitable for use in taking a blood sample during a blood collection procedure in which blood is collected from a donor via a needle line and delivered to a collection bag via a bag line, the apparatus comprising:

sample collection means, a sample line comprising said sample collection means or connected thereto, valve means having an inlet connected to the needle line for receiving blood from the donor, a first outlet connected to said sample line for conveying blood from the inlet to said sample collection means during sample collection, and a second outlet connected to the bag line for conveying blood from said inlet to the collection bag during blood collection, and valve actuator means having a first position for directing initial blood flow from the inlet to the first outlet to effect sample collection while preventing blood flow through said second outlet to the collection bag, and having a second position for directing initial blood flow from the inlet to the second outlet to effect blood collection while preventing blood flow through the first outlet.

6. Apparatus according to claim 5 wherein said valve actuator means can be positioned intermediate between said first and second positions, to prevent blood flow through both the first and the second outlet.

7. Apparatus according to claim 6 wherein:

said valve actuator means can be in a third position to prevent blood flow through both the first and the second outlets, said first, intermediate, second and third positions are reached sequentially by moving said actuator means in one direction, and said valve means includes non-return means adapted to prevent said actuator means from moving said actuator through said positions in reverse sequence from a higher number position to a lower number position.

8. Apparatus according to claim 5 wherein:

the valve means includes a body having a cylindrical chamber incorporating said inlet and said first and said second outlet, the inlet and outlets being in fluid connection with said chamber, the actuator means includes a cylindrical rotor located within said chamber for rotation therein, the rotor having a cylindrical periphery, said rotor includes a first and second channel each extending through the rotor and each having ends that open into said periphery, there being no connection between said first and second channels within the rotor, and the arrangement of said channels is such that, when the actuator means is in said first position, the rotor is arranged in the chamber so that the first channel connects the inlet with the first outlet and, when the actuator means is said second position, the rotor is arranged within the chamber so as that the second channel connects the inlet to the second outlet.

9. Apparatus according to claim 8 wherein:

said rotor has an end face, a sampling port on said end face and a third channel connected to said port and opening into said periphery, the arrangement of said third channel is such that, when the actuator is in the second position, the third channel connects the first outlet with the sampling port so that blood contained in the sample line is accessible via the sampling port while blood is flowing from the inlet through the second channel to the second outlet, when the apparatus is in use.

10. Apparatus according to claim 5 wherein:

the valve means includes body having a longitudinally extending cylindrical bore therein said second outlet and said inlet extend laterally into said body so as to connect with said bore, the actuator means comprises a cylindrical member fitted within the bore for longitudinal and rotary movement relative to the body, said member comprising the aforesaid actuator and having a cylindrical side face and an end face, said member has a first channel therein that extends axially and opens into said end face to form said first outlet, said first channel also opening into said side face of the member, said member has a second channel formed therein that extends laterally across the member but is not in fluid connection with said first channel, and the arrangement of the first and second channels is such that, when the actuator is in said first position, the inlet is connected by the first channel to the first outlet and, when the actuator is in the second position, the inlet is connected by the second channel to the second outlet.

11. Apparatus according to claim 10 wherein:

movement of the actuator from the first to the second position is effected by both axial and rotational movement of the member to align the second channel with the inlet and the second outlet, and a sample port is provided in the body so that, when the actuator is in the second position, said port is connected by the first channel with the first outlet so that blood in the sample line can be conveyed to the sample port for sampling while blood collection is taking place via the second outlet and the bag line.

12. Apparatus according to claim 5, wherein:

said sample and bag lines are connected directly to the needle line at a junction of said lines, said valve means includes a body through which part of the sample line and a part of the bag line pass through and exit from said valve means, said needle line at or near said junction forming the inlet of the valve means, said part of the sample line is formed from resilient tubing that can be collapsed to effect closure of said sample line, and said part of the sample line includes a portion that exits from the body thus forming said first outlet of said valve means, said part of the bag line is formed from resilient tubing that can be collapsed to effect closure of said bag line, and said part of the bag line includes a portion that exits the body thus forming said second outlet of the valve means, said actuator means can be in said first position to collapse the tubing of the bag line but not the tubing of the sample line so that blood can flow from the needle line to said sample line, and said actuator means can be in said second position to collapse the tubing of the sample line but not the tubing of the bag line so that blood can flow from the needle line to the bag line.

13. Apparatus according to claim 12 wherein said valve actuator means can be positioned intermediate between said first and said second positions to collapse both said part of the sample line and said part of the bag line to prevent blood flow through the sample line and blood flow through the bag line.

14. Apparatus according to claim 13 wherein:

said valve actuator means can be in a third position, to prevent blood flow through both the first and second outlets, said first, intermediate, second and third positions are reached sequentially by moving said actuator means in one direction, and said valve means includes non-return means that can prevent the actuator means from moving the actuator through said positions in reverse sequence from a higher number position to a lower number position.

15. Apparatus according to claims 14 wherein:

said part of the sample line and said part of the bag line are arranged in substantially parallel spaced relation within said valve means, and the actuator means comprises rollers arranged to move linearly within said valve means with said rollers rolling on said part of said sample line and on said part of said bag line to selectively collapse said lines to effect operation of said valve means.

16. Apparatus according to claim 12 wherein:

said part of the sample line and said part of the bag line are arranged in spaced coplanar relation on opposite sides of a circle formed on a platten or base in said valve means, the circle having a center, and the actuator comprising a carriage mounted for rotation about said center and in a plane substantially parallel to said coplanar parts of said sample and bag lines, and said actuator having rollers to selectively bear upon said parts of said sample and bag lines to. effect the operation of said valve means by rotation of the carriage and by selective compression of said parts of said sample and bag lines.

17. A multi-position valve for blood collection, comprising:

a body having an inlet, a first outlet and a second outlet, and actuator means moveable in sequence to (i) a first position wherein said first outlet is connected to said inlet but said second outlet is not connected to said inlet, (ii) an intermediate position wherein neither said first nor said second outlet is connected to said inlet, (iii) a second position wherein said second outlet is connected to said inlet but said first outlet is not connected to said inlet, and (iv) a third position wherein neither said first nor said second outlet is connected to the inlet.

18. A multi-position valve according to claim 17 having non-return means that can be positioned between said actuator means and said body to constrain said actuator means to move only in the aforesaid sequence and not in a reverse sequence.

19. A multi-position valve according to claim 17 having stop means that can be positioned between said actuator and said body to prevent said actuator means from moving beyond said third position.

20. A multi-position valve according to claim 17 having a sample port through which samples of blood may be drawn through said first outlet from said sample collection means, when said actuator is in said second position and said valve is in use.

21. A multi-position valve according to claim 17 further comprising an attachment means whereby said valve can be releasably attached to said arm of a donor during a blood collection procedure.

* * * * *